(12) United States Patent
Bay et al.

(10) Patent No.: US 7,696,326 B2
(45) Date of Patent: *Apr. 13, 2010

(54) MULTIPLE ANTIGEN GLYCOPEPTIDE CARBOHYDRATE, VACCINE COMPRISING THE SAME AND USE THEREOF

(75) Inventors: Sylvie Bay, Paris (FR); Daniele Cantacuzene, Paris (FR); Claude Leclerc, Paris (FR); Richard Lo-Man, Paris (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/619,457

(22) Filed: Jan. 3, 2007

(65) Prior Publication Data

US 2007/0098730 A1  May 3, 2007

Related U.S. Application Data

(62) Division of application No. 09/049,847, filed on Mar. 27, 1998, now abandoned.

(60) Provisional application No. 60/041,726, filed on Mar. 27, 1997.

(51) Int. Cl.
*C12P 21/02* (2006.01)
*C07H 21/04* (2006.01)

(52) U.S. Cl. ............ 530/387.7; 530/387.5; 530/387.1; 530/350; 530/322; 536/1.11

(58) Field of Classification Search ............ 530/387.7, 530/387.5, 387.1, 350, 322; 536/1.11
See application file for complete search history.

(56) References Cited

U.S. PATENT DOCUMENTS

| 4,386,026 A | 5/1983 | Ponpipom et al. |
| 5,229,490 A | 7/1993 | Tam |
| 5,580,563 A | 12/1996 | Tam |
| 5,679,352 A * | 10/1997 | Chong et al. ............ 424/256.1 |
| 5,807,559 A * | 9/1998 | Jondal ...................... 424/278.1 |
| 2002/0044937 A1* | 4/2002 | Birnstiel et al. .......... 424/178.1 |

OTHER PUBLICATIONS

Lett et al, Infection and Immunity, 1995, 63(7), 2645-51.*
Fung et al, Cancer Research, 50, 4308-14, 1990.*
Lo-Man, R., et al., "A Fully Synthetic Therapeutic Vaccine Candidate Targeting Carcinoma-Associated Tn Carbohydrate Antigen Induces Tumor-Specific Antibodies in Nonhuman Primates," Cancer Research, vol. 64, July 15, 2004, pp. 4987-4994.
Longenecker, et al., Ann. New York Academy of Sciences, 1993, vol. 690, pp. 279-291.
Zanini, at al., Bioconpugate Chemistry, 8, pp. 187-192 1997.
Bay, et al., J. Pep. Res. 49, pp. 620-625, 1997.
Kuduk, S. D., et al., "Synthetic and Immunological Studies on Clustered Modes of Mucin-Related Tn and TF O-Linked Antigens: The Preparation of a Glycopeptide-Based Vaccine for Clinical Trials Against Prostate Cancer," J. Am. Chem. Soc., vol. 120, 1998, pp. 12474-12485.
Haworth, W. N., et al., "Polysaccharides," J. Chem. Soc., 1937, pp. 784-791.
Lett, E., et al., "Immunogenicity of Polysaccharides Conjugated to Peptides Containing T- and B-Cell Epitopes," Infection and Immunity, Mar. 1994, pp. 785-792.
Sigma-Aldrich Fine Chemicals, Alphabetical List of Compounds, p. 671.

* cited by examiner

*Primary Examiner*—T. D. Wessendorf
(74) *Attorney, Agent, or Firm*—Oblon, Spivak, McClelland, Maier & Neustadt, L.L.P.

(57) ABSTRACT

The invention of the present application relates to a method for obtaining antibodies directed against a carbohydrate moiety contained in a carbohydrate peptide conjugate, by administering to a subject a composition containing a carbohydrate peptide conjugate and collecting the antibodies directed against the said carbohydrate moiety from a serum previously obtained from the subject.

1 Claim, 7 Drawing Sheets

B = carbohydrate, or carbohydrate and tumor peptidicmarker
T = T, $CD_4^+$ epitope
K = lysine a = B4 - T4 - M
b = B8 - T8 - M
c = B2 - T2 - M
d = B4 - T4 - M (different organization of T - B epitope)

A

1: $R_1$ = Ac, $R_2$ = t-Bu, $R_3$ = Fmoc, $R_4$ = H or $CH_3$
2: $R_1$ = $R_2$ = H, $R_3$ = Fmoc, $R_4$ = H or $CH_3$
3: $R_1$ = $R_2$ = $R_3$ = H, $R_4$ = H or $CH_3$

B

1: $R_1$ = Ac, $R_2$ = t-Bu, $R_3$ = Fmoc
$R_4$ = H or $CH_3$
$R_5$ = SUGAR MOIETY
2: $R_1$ = $R_2$ = H, $R_3$ = Fmoc
$R_4$ = H or $CH_3$
$R_5$ = SUGAR MOIETY
3: $R_1$ = $R_2$ = $R_3$ = H
$R_4$ = H or $CH_3$
$R_5$ = SUGAR MOIETY

SEQUENCE LISTING

<160> NUMBER OF SEQ ID NOS: 8

<210> SEQ ID NO 1
<211> LENGTH: 15
<212> TYPE: PRT
<213> ORGANISM: Clostridium tetani

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 21
<212> TYPE: PRT
<213> ORGANISM: Clostridium tetani

<400> SEQUENCE: 2

Phe Asn Asn Phe Thr Val Ser Phe Trp Leu Arg Val Pro Lys Val Ser
1               5                   10                  15

Ala Ser His Leu Glu
            20

<210> SEQ ID NO 3
<211> LENGTH: 12
<212> TYPE: PRT
<213> ORGANISM: Clostridium tetani

<400> SEQUENCE: 3

Gly Gln Ile Gly Asn Asp Pro Asn Arg Asp Ile Leu
1               5                   10

<210> SEQ ID NO 4
<211> LENGTH: 13
<212> TYPE: PRT
<213> ORGANISM: Poliovirus

<400> SEQUENCE: 4

Lys Leu Phe Ala Val Trp Lys Ile Thr Tyr Lys Asp Thr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Tyr Ile Lys Ala Asn Ser Lys Phe Ile Ile Gly Ile Thr Glu Leu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      TT1 peptide

<400> SEQUENCE: 6

Tyr Ile Lys Ala Asn Ser Lys Phe Ile Ile Gly Ile Thr Glu Leu
1               5                   10                  15

```
<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence:
      Carbohydrate peptide conjugate
<220> FEATURE:
<221> NAME/KEY: MOD_RES
<222> LOCATION: (1)
<223> OTHER INFORMATION: Beta-Gal-(1-3)-alpha-GalNac-Ser or Thr
<220> FEATURE:
<221> NAME/KEY: MOD_RES
<222> LOCATION: (3)..(15)
<223> OTHER INFORMATION: This region may encompass 1-13 Lysine residues
<220> FEATURE:
<221> NAME/KEY: MOD_RES
<222> LOCATION: (17)
<223> OTHER INFORMATION: Beta-Gal-(1-3)-alpha-GalNac-Ser or Thr

<400> SEQUENCE: 7

Xaa Lys Lys Lys Lys Lys Lys Lys Lys Lys Lys Lys Lys Lys Lys
  1               5                  10                  15

Xaa

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      Tn6-T peptide
<220> FEATURE:
<221> NAME/KEY: MOD_RES
<222> LOCATION: (1)..(3)
<223> OTHER INFORMATION: alpha-GalNac-Ser or Thr
<220> FEATURE:
<221> NAME/KEY: MOD_RES
<222> LOCATION: (5)..(7)
<223> OTHER INFORMATION: alpha-GalNac-Ser or Thr

<400> SEQUENCE: 8

Xaa Xaa Xaa Gly Xaa Xaa Xaa Gly Lys Leu Phe Ala Val Trp Lys Ile
  1               5                  10                  15

Thr Tyr Lys Asp Thr
              20
```

US 7,696,326 B2

MULTIPLE ANTIGEN GLYCOPEPTIDE CARBOHYDRATE, VACCINE COMPRISING THE SAME AND USE THEREOF

TECHNICAL BACKGROUND

1. Field of the Invention

The present invention is directed to the field of immunotherapy and more particularly to a glycoconjugate, a composition and vaccine comprising the same and to the use thereof for enhancing the immune response and notably in cancer therapy and in therapeutic of infection caused by pathogenic agent against whom a humoral or a cellular immune response is necessary. The invention relates also to a diagnosis kit and a method for diagnosis of cancer.

2. Prior Art/Relevant Literature

As a result of aberrant glycosylation, cancer-associated carbohydrate antigens are exposed at the surface of tumor cells whereas they are hidden in normal cells (Ref. 1). Recent advances in immunology and in the identification of tumor specific antigens have renewed the interest for the development of cancer vaccines, and these exposed glycosidic B-cell epitopes have been considered as attractive targets for immunotherapy named "Active Specific Immunotherapy" (ASI) by Longenecker (Ref. 2). This approach involves immunization with a defined antigen to elicit a specific immune response to that antigen and could represent an alternative to the conventional cancer therapies.

Among the large number of known tumor markers, the Tn (a-GalNAc-Ser/Thr). the T* (b-Gal-(1→3)-a-GalNAc-Ser/Thr) and the sialosyl-Tn (a-NeuAc-(2→6)-a-GalNAc-Ser/Thr) antigens have been extensively studied since they are expressed on mucin-type glycoproteins by the majority of adenocarcinomas (Ref. 3), Indeed, several studies have shown some protection against tumors after immunization with these glycosidic antigens, in experimenital or clinical studies. These tumour associated carbohydrates are relevant markers for cancer diagnostic and prognosis (Ref. 34). Using desialyated red blood cells, which are rich in T and Tn determinants, Springer observed a long-term effective protection against recurrence of human breast carcinoma (Ref. 3c, Ref. 4). An other group investigated the potential of ASI with desialylated ovine submaxillary mucin (d-OSM), which contains high density of the Tn epitope; their studies showed that this antigen provided a good protection and a long-term survival in mice with mammary carcinoma (Ref. 5). Partially-d-OSM also gave efficient protection against human colon carcinoma (Ref. 6). Ratcliffe et al. were the first to use a synthetic tumor-associated antigen, a T antigen-protein conjugate, to stimulate an efficient immune response in rabbits (Ref. 7). Thereafter Longenecker extensively studied similar synthetic carbohydrate hapten conjugates and found that they induce an increased survival of mice grafted with mammary carcinoma cells (Ref. 8, and of patients with ovarian cancers (Ref. 9). Similar studies of the same group have further shown an increased protection of patients suffering from breast cancer (Ref. 10) or melanoma (Ref. 11) after respective administration of sialosyl Tn- or the GM2 ganglioside-protein conjugates. On the other hand, Toyokuni et al. generated an anti-tumor antibody response in mice after immunization with a Tn antigen coupled either to OSA (Ovine Serum Albumin) or to a synthetic lipopeptide (Ref. 12). This last result was interesting since it was the first example of a small synthetic carbohydrate antigen that generates an immune response against a tumor associated carbohydrate antigen, without the use of a macromolecular carrier or adjuvants.

These studies suggested that carbohydrate antigens are appropriate candidates for anti-tumor vaccine development. However, carbohydrate antigens do not possess T-cell epitope and therefore induce only weak T cell-independent antibody response. Several approaches have been explored to increase the immunogenicity of such carbohydrates. The use of biological material which expresses clusters of antigens on a protein backbone (like desialylated red blood cells or OSM) is a possibility. But the most widely used approach is to conjugate the carbohydrate to a carrier protein, such as Bovine serum albumin (BSA) or Keyhole limpet hemocyanin (KLH).

Although these immunogens have shown some promise, protein carriers display major disadvantages. The grafted epitope represents only a small part of the total conjugate and it is distributed at random on the carrier surface. Therefore, immune responses to the carrier molecule may result in a low level of the desired antibodies as compared to the total amount of antibodies produced. Moreover, these conjugates present ambiguity in both composition and structure and they do not always induce reproducible immune response. Recent advances in the total synthesis of oligosaccharides expressed by tumour cells (Ref. 35. Ref. 36) open new possibilities for such achievement. However, haptenic molecules such as carbohydrates require their association in more complex structures to stimulate immune responses. The use of traditional protein conjugates raises the problem of hapten-specific suppression (Ref. 37. Ref. 38), and their poorly defined chemical composition and structure may limit their efficacy.

Until now, as for chemically defined structures, dendrimeric poly-lysine backbones, which will be described in more detail later in the present specification, have been widely used for presenting peptides (Ref. 14). However, to our knowledge, there is only one preliminary attempt of their utilisation for presenting carbohydrates to the immune system (Ref. 16). This latter reference teaches the synthesis of three sialylated multiple antigen peptides having tetanus toxin T-cell epitopes. However a response against the T cell epitope only was obtained, but not against the B cell epitope. A similar strategy was also recently published (Ref. 17) where the authors coupled mixtures of natural polysaccharides obtained from *Streptococcus* and *Saccharomyces* to a Multiple Antigenic Peptidic system.

Thus, there still exist a need for a new conjugate circumventing the drawbacks mentioned above of the prior art constructions which has a chemically defined structure, is capable of stimulatiny both the antibody response and the T response when administered in a human or animal body while avoiding undesired immune responses.

SUMMARY OF THE INVENTION/PREFERRED EMBODIMENTS

Accordingly, the present invention is generally directed to a carbohydrate peptide conjugate comprising:

a carrier comprising a dendrimeric poly-Lysine enabling multiple epitopes to be covalently attached thereto, at least one peptide comprising one T epitope or several identical or different T epitopes at least one carbohydrate moiety containing B epltope, provided it is not a sialoside, or several identical or different B epitopes.

The peptide comprising the T epitope(s) can be bound to a lysine of said carrier, as the carbohydrate moiety containing B epitope(s).

This approach for presenting epitopes is herein referred to as the Multiple Antigen Glycopeptide (MAG). The conjugate of the present invention is notably useful for enhancing the antibody response in a human or animal body to which it has been administered and in particular as a vaccine.

Moreover, since a multiple antigenic O-linked glycopeptide (MAG), according to the present invention, carrying for example the carbohydrate Tn antigen associated with a CD4+ T cell epitope was shown able to induce anti-Tn IgG antibodies which recognise human tumour cell lines, accordingly the present invention also concerns an composition capable of increasing the survival of a tumour-bearing human or animal. A therapeutic immunisation protocol performed with this fully synthetic immunogen increased the survival of tumour-bearing mice.

More particularly the present invention is directed to a carbohydrate peptide conjugate comprising;
  at least 3 lysine residues covalently bound to each other.
  at least one peptide comprising a T epitope bound to a lysine residue, and
  at least one carbohydrate moiety containing epitope B, optionally substituted, covalently linked to the end of said peptide opposite to lysine, and with the proviso that said carbohydrate moiety is not a sialoside radical.

According to another embodiment of the invention, the conjugate comprises:
  at least one peptide comprising one T epitope, or several identical or different T epitopos, and
  at least one carbohydrate moiety, or a derivative thereof, containing B epitope, provided it is not sialoside, or several identical of different epitopes.

Another object of the present invention is a pharmaceutical composition comprising the conjugate of the present invention.

A further object of the present invention is a vaccine comprising the conjugate according to the present invention.

A still further object of the present invention is a method of enhancing the immune response of a human or animal body in particular B and/or T-cell responses, wherein the conjugate according to the present invention is administered to said human or animal body.

Another object of the present invention is a method of inducing B-cell responses against saccharidic epitopes in a human or animal body, wherein the conjugate according to the invention is administered to said human or animal body.

A still further object of the present invention is a method of vaccination of a human or animal body wherein the conjugate according to the present invention is administered to said human or animal body.

Another object of the present invention is a diagnosis kit comprising antigen specific antibodies elicited by immunization of a human or animal body with a composition according to the present invention.

A further object of the present invention is a method of diagnosis of cancer wherein a biological sample is bringing into contact with at least one of these antibodies and wherein one determines the formation of complexes between this antibody and molecules comprised in the said sample.

A still further object is an immunogenic composition as described hereabove, capable to elect an immune response against a viral infection caused by a pathogen such as hepatitis virus, HIV or CMV.

The present invention will now be described in details in the following description with reference to the drawings below.

DETAILED DESCRIPTION

Definitions and Abbreviations

Figure 1:
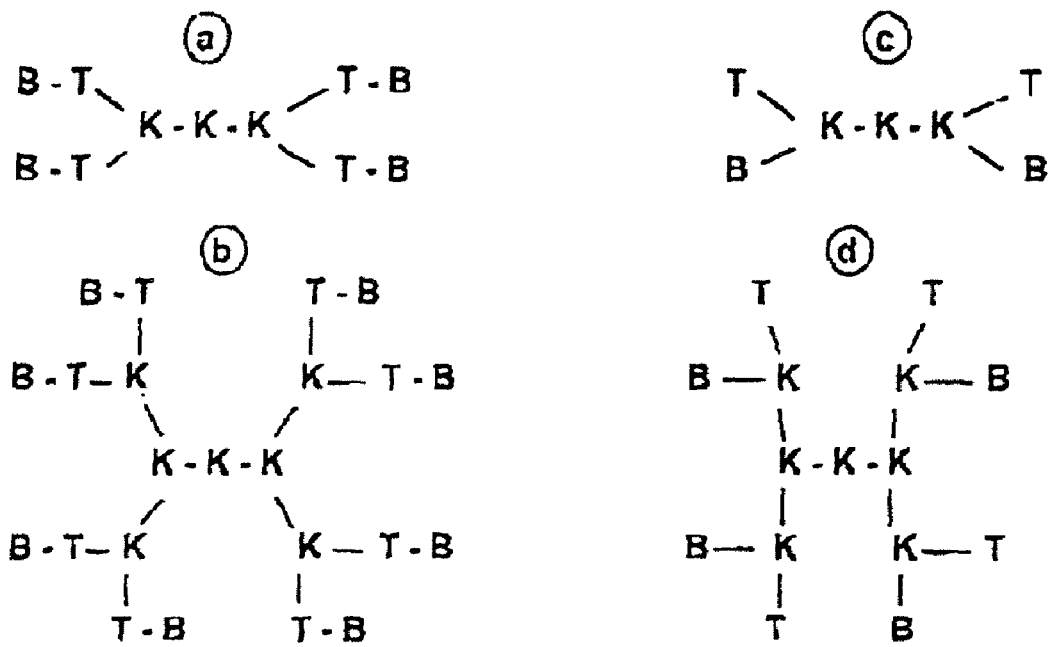
FIG. 1 is a schematic representation of a MAG compounds (B4-T4-M, B8-T8-M, B2-T2-M and B4-T4-M (with different organization of T and B epitopes) (a to d), tri-Tn(e) and hexa-Tn(f) according to the present invention.
Figure 1:
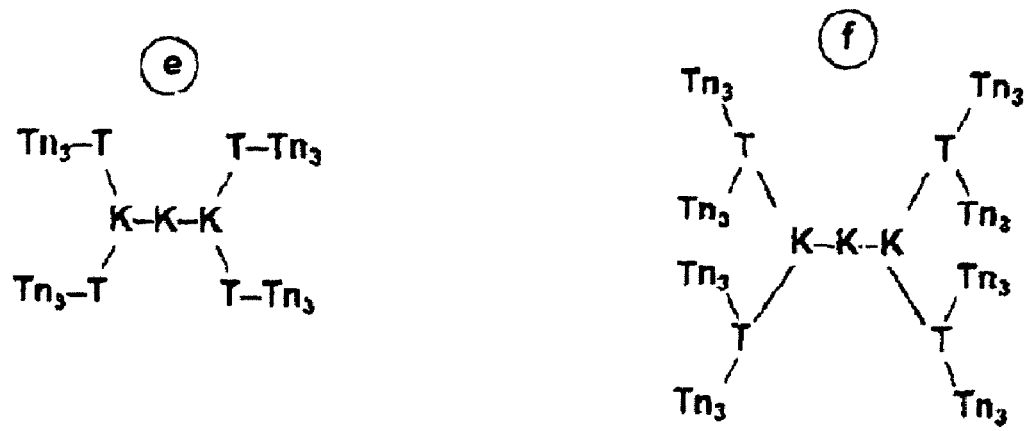

Antigens:

The expressions carbohydrate B antigen, B epitope, B-cell antigen, B-cell epitope are used herein to designate in general glycosidie antigens capable of eliciting a B-cell response, the antigens consisting of sialosides being excluded.

By T antigen or T epitope, T-cell antigen, T-cell epitope is meant an antigen generally of a peptidic nature capable of eliciting a T cell response.

Synthetic compounds B-T, M, B4-M, T4-M and B4-T4-M were also used as antigens (see Table hereafter).

The abbreviation M as used herein is an example of MAP (Multiple antigen peptide and designates the following structure:

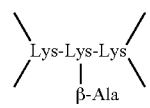

Where appropriate, the universal one letter code for aminoacids was used herein (K for lysine, etc.).

Other abbreviations also used in the present invention:

BSA, bovine serum albumin; OSA, ovine serum albumine; Ova ovalbumin; OSM, ovine submaxillary mucin; d-OSM, desialylated ovine submaxillary mucin; ES MS, electrospray mass spectrometry; Fmoc, Fluoren-9-yl-methoxycarbonyl; PBS, phosphate buffered saline.

The expression <<antibody response>>, <<B- or B-cell response>> are used indistinctively herein. The same applies to <<cellular response>>, <<T- or T-cell response>>.

The present invention is directed in its primary aspect to a carbohydrate peptide conjugate comprising:
  an appropriate carrier based on a dendrimeric poly-Lysine enabling multiple epitopes to be covalently attached thereto,
  at least one peptide comprising one T epitope or several identical or different T epitopes,
  at least one carbohydrate moiety containing B epitope, provided it is not a sialoside or several identical of different B epitopes.

Several identical T or B epitopes means between two and eight of the same epitope.

Several different T epitopes means between two and eight of T epitopes from different origins.

Several different B-epitopes means between two and eight of B-epitopes from different origins.

The poly-Lysine core of the present conjugate is called a dendrimer because it may be represented (FIG. 1) as a star with multiple branches all substantially identical.

As stated earlier multiple antigen peptide system have been described in 1988 by Tam (Ref. 13) that are based also on certain dendrimeric structure in which peptidic antigen are covalently conjugated to the branches of the latter.

Examples of suitable carriers comprise those having a structure based on a poly-Lysine core forming a multiple branches star, such as, for example a 8 or 4 branches star.

Thus the present invention in one of its preferred embodiment is directed to a conjugate comprising a dendrimeric structure based on a poly-Lysine core forming a 4 branches star, with an epitope T covalently bound to each of the branches and associated to a carbohydrate moiety (provided it is not a sialoside radical) containing an epitope B.

According to a further preferred embodiment of the present invention the multiple antigen glycupeptide (MAG) forming the conjugate according to the present invention comprises at least 3 lysines and up to 15 lysines residues covalently linked to one another. Most preferably the present conjugate comprises 3 lysines.

In a preferred embodiment, to the NH2 end of each lysine residue is bound at least one peptide comprising one epitope T bound to a lysine and at least a carbohydrate residue, being not a sialoside, optionally substituted, covalently bound to the end of said peptide opposite to the lysine and forming a B epitope.

In another preferred embodiment, to the $NH_2$ end of each lysine residue is bound at least one carbohydrate residue, being not a sialoside, optionally substituted and forming a B-epitope bound to a lysine and at least a peptide comprising one T-epitope covalently bound to the end of said carbohydrate opposite to the lysine.

The MAG structure referred to herein will be better understood by reference to FIG. 1.

In FIG. 1 are schematically represented examples of a 4 to 8 branches star comprising from 3 to 7 lysines bearing 4 to 8 aminogroups bound to desired epitopes (epitopes B, optionally substituted with a peptide and epitopes T). This structure provides a high density of the antigens at the surface of the lysine core.

Moreover this structure offers several advantages. First, the carbohydrate content is much higher in the MAG system (usually over 90%) than in the traditional protein conjugates. This structure of high density glycopeptide antigens induce higher antibody responses confirming the previous observation comparing an MAP system to the same antigens covalently linked to a carrier protein (Ref. 13b, Ref. 14).

A further advantage of the MAG is that the core matrix, representing a minor fraction of the total construct has a low immunogenicity, thus avoiding undesired immune responses (Ref. 13a). Another advantage of the present construct is that the resulting synthetic immunogen has a well defined chemical structure.

The presence of both carbohydrate B epitopes and T epitopes on the glycoconjugate of the present invention renders the latter an efficient immunogen as will be demonstrated later in the experimental section.

The carbohydrate moiety, containing the epitope B of the conjugate according to the present invention, may originate, for example, from tumor (cancer) glycosidic antigens of:

the glycolipid class, including acidic glycolipid such as, for example, gangliosides GD2, GD3 and GM3 (melanoma) and neutral glycolipids such as, for example. the Lewis$^y$ (Le$^y$) (breast, prostate, ovary) and the Globo H (breast, prostate, ovary) antigens. The sialylated derivatives belonging to this class are excluded.

the O-glycosyl peptides (or aminoacid) class such as, for example, the Tn antigen (αGalNAc-Ser or αGal NAc-Thr), T* antigen (β-Gal-(1-3)-α-GalNac-Ser or βGal(1-3)αGal-NAc-Thr), two tumor markers frequency present in carcinomas but not usually in normal tissues [Splifiger G. F. Science 224, 1198-1206 (1984)] (ovary, breast, lung), or di-Tn (α GalNAc-Ser/Thr)$_2$, tri-Tn(α GalNac-Ser/Thr)$_3$ or hexa-Tn(αGalNAc-Ser/Thr)$_6$.

The epitope B of the conjugate according to the present invention may also originate from capsular bacterial polysaccharides of, for example, *Neisseria meninqitis, Haemophilus influenzae, Streptococcus pneumoniae*, and of the *Streptococcus* group, with the exception of the sialylated polysaccharides.

The polysaccharides are carbohydrate residues obtained by synthetic process.

The epilope B of the present conjugate may be also of fungal origin, such as for example, onc isolated from the yeast *Saccharomyces*.

The B epitope of the conjugate according to the present invention are preferentially tumor markers, such as, for example, Tn and T* antigens.

The preferred carbohydrate moiety forming the B epitope of the conjugate according to the present invention may be comprised of a galautosyl residue, or a derivative thereof, being not sialylated.

It can be selected from the group comprising Tn, di-Tn, tri-Tn, hexa-Tn, or T* antigens.

Thus in one of its preferred embodiment the invention relates to a carbohydrate peptide conjugate comprising:

at least 3 lysine residues covalently bound to each other, at least one peptide comprising a T epitope bound to a lysine residue, and at least one galactosyl residue, optionally substituted, covalently linked to the said peptide and forming epitope B with the proviso that said carbohydrate moiety is not a sialoside radical.

In a related aspect of this embodiment the galactosyl residue is substituted by another glycosyl residue.

In a related aspect, the conjugate of the present invention comprises 3 lysine residues, at least 4 epitopes of the T type, which may be the same or different linked to the NH$_2$ ends of 2 of the lysine residues, and 4 α-galactosyl-Nacetyl-Serine residues.

The carbohydrate moiety of the conjugate of the present invention may further be grafted on the dendrimeric structure in combination with one or more tumor peptidic CD3$^+$ cell epitopes recognized by tumor-specific cytotoxic T cells. These peptidic CD3$^+$ T cell epitopes recognized as tumoral markers may be selected in the group consisting of:

MUC-1 peptides (pancreas, breast)

MAGE 1 and 3 (melanoma, lung) (T. Boon et al. (1995). Immunology Today, vol. 16 no7.pp 334-336)

pme117/gp 100 (melanoma)

Tyrosinase (melanoma)

BAGE (melanoma)

GAGE (melanoma)

LB-33-B (melanoma)

CDK4
p185$^{HER}$ (breast, ovary)
CEA
MART1/Melan-A (melanoma)
or selected in the group consisting of tumor antigens described in A. Van Pel et al. (1995) Immunological Reviews no 145, pp 229-250 or in P. G. Coulie (1995), Stem Cells, 13, pp 393-403.

As mentioned earlier, in the conjugate of the present invention a CD4$^+$ T epitope is conjugated to a carbohydrate B epitope described above to elicit an efficient immune response.

Such an epitope can comprise between almost 5 and 50 amino-acids.

One such preferred T epitope is the CD4$^+$, T epitope which is the synthetic peptide that corresponds to the 103-115 sequence of VP1 protein from poliovirus type 1 or alternatively it may be a peptide comprising the CD4$^+$, T epitope selected from the group comprising:
  fragments of the Tetanus toxin such as, for example:
    830-844 sequence of the tetanus toxin (QYIKANSKFIGITEL; SEQ ID NO: 1)
    947-967 sequence of the tetanus toxin (FNNFTVSFWLRVPKVSASHLE; SEQ ID NO: 2).
    1273-1284 sequence of the tetanus toxin (GQIGNDPNRDIL; SEQ ID NO: 3)
  fragments of pneumococcal type 4 polysaccharide, and oligosaccharide tetanus toxoid conjugates as described by C. C. A. M. Peeters (1991), in The Journal of Immunology, 146, 4309-4314,
  meningococcal liposaccharides as described by A. F. M. Verheul (1991) in Detection and Immunity, vol.59, no 10, pp. 3566-3573.

These peptidic T epitopes typically bind to a plurality of MHC (Major Histocompatibility Complex) human and murine molecules of class II avoiding in consequence the restriction problems encountered with the CD4$^+$, T cellular response, associated with the polymorphism of the MHG molecules existing between individuals. Moreover the use of tetanus toxin peptides should increase the immunogenicity of antigens present on the conjugate of the present invention, as a result of the vaccination of numerous individuals with the tetanus toxoid.

According to another embodiment of the invention, the conjugate comprises:
  at least one peptide comprising one T epitope, of several identical or different T epitopes, and
  at least one carbohydrate moiety, or a derivative thereof, containing B epitope, provided it is not sialoside, or several identical of different epitopes.

Said conjugate can be Tn3-T, wherein T can be a poliovirus or tetanus antigen. It can be also Tn6-T, wherein T is a poliovirus antigen having the following sequence KLFAVWKITYKDT (SEQ ID NO: 4).

The formula of Tn6-T is thus:
  (Tn$_3$-G)$_2$ KFLAVWKITYKDT (SEQ ID NO: 4, wherein Tn$_3$ is a linear trimer of (α GalNAc Ser), or (α GalNAc Thr).

They can be obtained by peptidic synthesis, wherein a peptidic bound is created between the glycosylated serine, or threonine, and the peptide T.

As stated earlier the invention is also directed to a pharmaceutical composition comprising a conjugate according to the present invention. Such composition comprises an effective amount of the present conjugate for example in a pharmaceutically acceptable vehicle and may be of liquid or emulsion form, in the presence or not of an adjuvant (including aluminium hydroxyde and cytokines). The route of administration of the said composition may be any of usually used route (including intra-tumoral administration such as injection). The said immunogenic composition comprising at least one carbohydrate peptide conjugate, wherein said conjugate comprises various carbohydrate antigens can be used to induce a more efficient anti-tumour immunity against cancers.

The amount of conjugate can be comprised between 10 μg and 1 ng.

The present invention is also directed to a vaccine comprising a conjugate according to the present inventon.

A further object of the present invention is a method of enhancing the immune response of a human or animal body, notably the T- and/or B-cell mediated response, in particular against bacteria, wherein the conjugate of the present invention is administered to said human or animal body.

A still further object of the present invention relates to a method of inducing a B-cell response in a human or animal body wherein at least one conjugate according to the invention is administered.

The invention also relates to a method of inducing a B-cell response in a host characterized in that in said host is administered at least one carbohydrate peptide conjugate comprising:
  at least 3 lysine residues covalently linked to one another,
  at least one peptide comprising a T epitope linked to a lysine residue, and
  at least one carbohydrate moiety optionally substituted, being not a sialoside.

Another object of the present invention concerns a method of vaccination of a human or animal body wherein a conjugate according to the present invention is administered to said human or animal body.

A still further object of the present invention is a diagnosis kit comprising antigen specific antibodies elicited by immunization of a human or animal body with a composition according to the present invention.

Such antibodies are also considered as subjects of the present invention. They can be used in a method of diagnosis of cancer comprising bringing into contact at least one of these antibodies with a biological sample and determining the formation of complexes between this antibody and molecules comprised in this sample.

The present invention will now be illustrated in more details by the following examples and should not be intended to be limited thereto.

EXAMPLES

Example 1

Synthesis of the Glycoconjugate According to the Invention

The strategy for the construction of the MAG conjugate first involved the synthesis of the Tn antigen which represents the B-cell epitope. This glycosidic tumor marker was then conjugated to a poly-lysine core (M) in association with the peptidic CD4$^+$. T-cell epitope, giving the full construction B4-T-4-M. In addition the reference compounds which are necessary for the immunological tests were synthetized (B, T, B-T, B4-M, T4-M, M).

Figure 2:
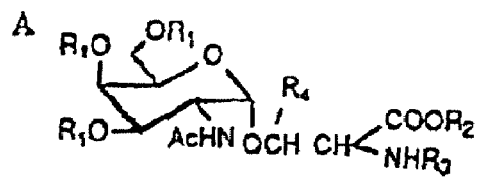
FIG. 2 depicts the Tn antigen and its derivatives.
Figure 2:
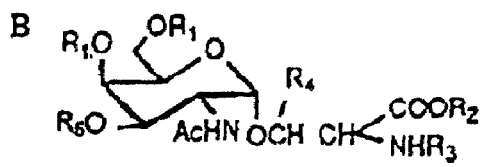
Figure 3:
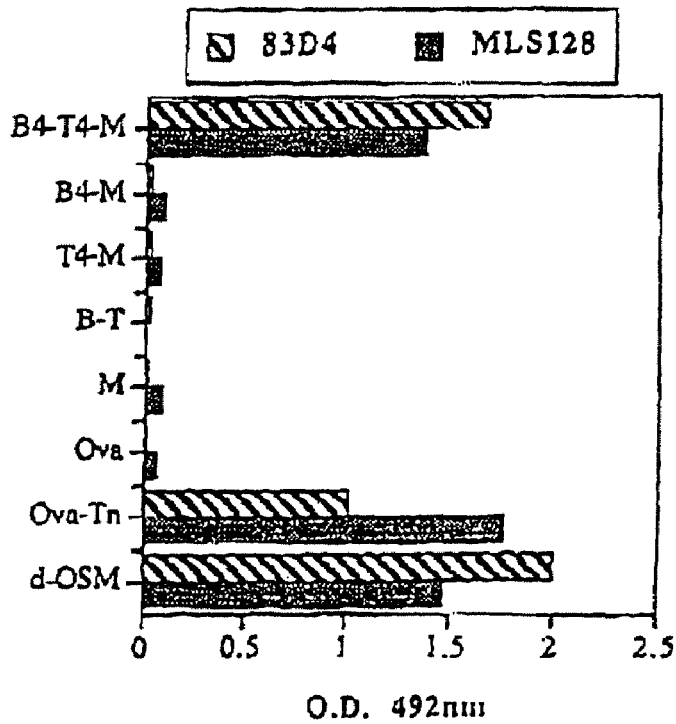
FIG. 3 shows the recognition of B4-T4-M by two anti-Tn monoclonal antibodies.

The synthesis of the Tn antigen 2 (FIG. 2) was performed by classical methods (Ref. 19, Ref. 20) starting from tri-O-acetyl-D-galactal (Ref. 21). N-(Fluorenylmethoxycarbonyl)-L-serine tert-butyl ester (Ref. 22) was used for the Koenigs-Knorr reaction with 3,4,6-tri-O-acetyl-2-azido-2-deoxy-b-D-galactopyranosyl chloride (Ref. 23), giving the protected derivative 1. The final deprotection of acetyl and of the t-butyl ester afforded in antigen 2 appropriately protected for the peptide synthesis.

B4-T4-M 4 was assembled by the conventional solid-phase peptide methodology using the Fmoc chemistry which is compatible with the glycopeptide synthesis. After attachment of the b-alanyl spacer on the Wang resin, the lysine core was constructed by coupling successively two levels of FmocLys (Fmoc)OH, providing four amino groups. The lysine core was further elongated by the appropriately protected amino acids of the poliovirus (KLFAVWKITYKDT; SEQ ID NO: 4) T epitope sequence, four copies of the same amino acid being sequentially added. Ultimately 2 was incorporated to the dendrimeric peptide as a building block.

Of interest was the incorporation of the Tn antigen derivative 2 which could be achieved with the fully deprotected sugar. This is very advantageous since it avoids the eventual side reactions (racemization and/or b-elimination) associated with the final deacetylation of the sugar residue. A few examples of the use of unprotected glycosidic units have already been reported (Ref. 24). After completion of the synthesis, the MAG 4 was released from the resin with aqueous trifluoroacetic acid (95%) and the peptide side-chains were simultaneously deprotected. No glycosldic cleavage is usually observed over a reaction time of 1.5 hours (Rcf. 25). A similar procedure was followed for the reference compounds. All the peptides and glycopeptides were characterized by amino acid analysis and electrospray mass spectrometry.

General Methods

For the synthesis of 2, reagents were purchased from Aldrich or Sigma. All the solvents were high grade and dry. $CH_2Cl_2$ was distilled over $CaH_2$ and toluene over sodium with benzophenone, before use. For the peptide synthesis, Fmoc-protected amino acid derivatives and Wang resin were obtained from Bachem or Novabiochem. The side chain of the aminoacids were protected by a t-butyl group except for tryptophan and the lysine residues of the T-epitope which were protected by a t-butyloxycarbonyl (Boc) group. DMF and acetonitrile for HPLC were purchased from Merck. The final compounds were purified by reverse phase high performance chromatography (HPLC) using a Perkin-Elmer pump system with a UV detector (230 or 280 nm). A column (250× 10 mm) of Nucleosil $C_{18}$ (5 mm, 300 Å) was used and the products were eluted with a gradient of MeCN/0.1% trifluoroacetic acid buffer during 20 min (flow rate 6 ml/min). $^1H$ NMR spectra (300.134 MHz, 3-(trimethylsilyl)propionic acid sodium salt as standard for spectra in $D_2O$) were recorded on a Bruker instrument. Mass spectra were measured by fast atom bombardment or by electrospray. Amino acid analyses were obtained using a Beckman 6300 analyser, after hydrolysis of the peptides with 6 N HCl (0.2% phenol was added when the peptide contains a tyrosifte residue) at 110° in sealed glass tubes for 20 h.

Solid Phase Synthesis, General Procedure:

The solid phase peptide and glycopeptide syntheses were performed manually using the standard Fmoc chemistry protocol (Ref. 40) on a polystyrene resin functionalized with p-benzyloxybenzyl alcohol (Wang resin). With the exception of the C-terminal b-alamine residue, the $N^a$-Fmoc amino acids (carrying standard side-chain protective groups) and the glycosylated building block 2 (3 equiv.) were incorporated to the peptide chain using TBTU as an activating agent and DMF as solvent. All the couplings were monitored by the Kaiser test (Ref. 29) and usually completed within 1 h. All Fmoc cleavages were carried out by treatment of the resin with 20% piperidine in DMF. Following each deprotection, the resin was successively washed with DMF, $CH_2Cl_2$, DMF. At the end of the synthesis, the resin was extensively washed with DMF and $CH_2Cl_2$, dried, and treated with an aqueous TFA solution for 2 h. After filtration of the resin, the solution was concentrated and the crude product precipitated with dietlhyl ether. The precipitate was filtered, dissolved in water and lyophilised. Peptides were purified on reverse phase HPLC (the elution conditions are indicted below, for each compound) and characterized by amino acid analyses and electrospray mass spectrometry.

$N^a$-(Fluoren-9-ylmethoxycarbonyl)-3-O-(2-acetamido-2-deoxy-a-D-galactopyranosyl)-L-serine 2:

$N^a$-(Fluoren-9-ylmethoxycarbonyl)-3-O-(2-acetamido-3,4,6-tri-O-acetyl-2-deoxy-a-D-galactopyranosyl)-L-serine tert-butyl ester 1 was prepared as previously described (Ref. 23) by glycosylation of $N^a$-(Fluoren-9-ylmethoxycarbonyl)-L-serine tert-butyl ester (Ref. 22) with 3,4,6-tri-O-acetyl-2-azido-2-deoxy-b-D-galactopyranosyl chloride (obtained from tri-O-acetyl-D-galactal) (21) using $Ag_2CO_3/AgClO_4$ as catalysts, followed by the reduction and acetylation of the 2-position (Ref. 19). The t-butyl ester of 1(2 g, 2.8 mmol) was then deprotected in formic acid (76 ml) (Ref. 20). The solution was stirred for 10 h and evaporated. The residue was dissolved in MeOH (200 ml) and the acetyl groups of the sugar moiety were removed by adding. dropwise, a solution of 1% MeONa (pH 11) (Ref. 46). After 15 h, the medium was neutralized by a Dowex 50WXB ($H^+$) resin and the final product 2 purified on a reverse phase column ($C_{18}$) using a gradient of water/MeCN: 1.27 g (yield 79%)

Reference Compounds:

M: The MAG syntheses require a low substitution of the resin. The preformed symetrical anhydride of $N^a$-Fmoc-bAla-OH (0.25 mmol) (30) was reacted with the Wang resin (1 g, 0.96 mmol/g) for 1 h, yielding a functionalization of approximatively 0.12 mmol/g as estimated by UV analysis of a resin sample (Ref. 31). After acetylation of the residual hydroxyl groups by $Ac_2O$ in DMF, the lysine core was assembled by sequential couplings of 0.48 and 0.96 mmol of $N^a$-Fmoc-Lys-(Fmoc)-OH. The cleavage of the peptide from the resin was carried out by TFA/water (95/5, 16 ml). The purification of the crude product by HPLC (gradient from 0% to 25%, 7.2 min retention time) gave M (94 mg). $^1H$-NMR ($D_2O$), d, 4.24, 4.03, 3.93 (3 CH a Lys), 3.54, 3.42 ($CH_2$—NH b-Ala), 3.22, 3 ($CH_2$ e Lys), 2.62 ($CH_2$—COOH b-Ala), 1.97-1.85 (2 $CH_2$ b Lys), 1.78-165 (2 $CH_2$ d, $CH_2$ b Lys), 1.58-1.3 (3 $CH_2$ g, $CH_2$ d Lys); ESMS: 473.2 (Calcd. 473.33).

T: The synthesis of the T epitope has been performed on 0.21 g of resin (0.15 mmol) by the general procedure. Cleavage of the resin-bound peptide (TFA/water/ethanedithiol: 95/2.5/2.5, 45 ml) and purification by HPLC (gradient from 0% to 65%, 12.6 min retention time) afforded T (31 mg). FABMS: $[M+H]^+$1613 (Calcd. 1611.9). Amino acid analysis: Ala 1.16 (1), Asp 1.03 (1), Ile 0.96 (1), Leu 1.01 (1), Lys 2.92 (3), Phe 1 (1), Thr 1.84 (2), Tyr 0.99 (1), Val 0.94 (1).

B-T: Further clongation of the T peptide chain (0.22 9 resin, 0.14 mmol, synthesized as above) was achieved with 2 as a building block. The glycopeptide was released from the resin (TFN/water/ethanedithiol: 95/2.5/2.5, 50 ml) and the crude product purified by HPLC (gradient from 10% to 60%, 11.2 min retention time) yielding B-T (63 mg). ESMS: 1903 (Calcd. 1903.22). Amino acid analysis: Ala 1 (1), Asp 1.05 (1), Ile 1.0 (1), Leu 1.05 (1), Lys 3.12 (3), Phe 1.05 (1), Ser 0.94 (1), Thr 1.97(2), Tyr 1.06(1), Val 1.0 (1).

B4-M: 2 was conjugated to the poly-lysine core (M) synthesized as described above (0.83 g resin, 0.1 mmol). After cleavage of the glycopeptide from the resin (TFA/water: 95/5, 25 ml), and purification by HPLC (gradient from 0% to 10%, 10.2 min retention time). B4-M was obtained (36 mg). ESMS 1633.9 (Calcd. 1633.78). Amino acid analysis: Lys 3 (3), Ser 4.06 (4).

T4-M: The lysine core M (0.25 g resin, 0.03 mmol, synthesized as above) was further elongated by the T epitope sequence. The cleavage of the peptide from the resin (TFA/water/ethanedithiol: 95/2.5/2.5, 25 ml) and its purification by HPLC (gradient from 12% to 45%, 16.5 min retention time) gave T4-M (67 mg). ESMS: 6852.08 (Calcd. 6853.35). Amino acid analysis : Ala 4 (4), Asp 4.4 (4), Ile 4 (4), Leu 4.1 (4), Lys 15.8 (15), Phe 4 (4), Thr 8.2 (8), Tyr 4.3 (4), Val 3.8 (4).

Multiple Antigen Glycopeptide B4-T4-M 4:

The synthesis of B4-T4-M was achieved by ultimately coupling 2 to T4-M (0.25 g resin, 0.03 mmol) which was obtained as described above. Cleavage of the glycopeptide was accomplished with TFA/water/ethanedithiol (95/2.5/2.5, 30 ml). After purification by HPLC (gradient from 10% to 65%, 11.9 min retention time), the target glycopeptide was obtained (25 mg). ES MS: 8014.09 (Calcd. 8014.45). Amino acid analysis: Ala 4 (4), Asp 4.78 (4), Ile 4.09 (4), Leu 4.15 (4), Lys 16.31 (15), Phe 4 (4), Ser 3.81 (4), Thr 8.58 (8), Tyr 4.5 (4), Val 3.63 (4).

Example 2

Immunological Results: Antigenicity and Immunogenicity of T,CD4$^+$-epitope and of Tn Antigen Within the Glycoconjugate MAG According to the Invention Materials and Methods:

Mice

Six to eight week-old female inbred mice were used in all experiments. BALB/c mice were from Iffa Credo (L'Abresle, France).

Antigen Presentation Assay:

For the dose response assays, $10^5$ T cell hybridomas 45G10 (specific for 103-115 poliovirus peptide) per well were cultured with $10^5$ A20 cells (ATCC, TIB-208 Rockville,. Md.) with different antigen doses for 24 h in RPMI 1640 medium supplemented with 10% Fetal calf serum, antibiotics 2 mM L-glutamine, $5\times10^{-5}$ M 2-mercaptoethanol. After 24 h, supernatants were frozen for at least 2 h at –70° C. $10^4$ cells/well of the IL-2 dependent CTLL cell line was cultured with 100 µl aliquot supernatant in 0.2 ml final volume. Two days later, [$^3$H] thymidine (0.3 µCi/well; AS=1 Ci/mmol) was added and the cells were harvested 18 h later with an automated cell harvester. Incorporated thymydine was detected by scintillation counting.

T-cell Proliferation Assay:

Mice were immunized subcutaneously with 10 µq of T, B-T, T4-MAP, B4-MAP or B4-T4-MAP compounds emulsified in complete Freund's adjuvant. Ten days later, lymph node (LN) cells were removed and single cell suspensions were prepared and cultured in HL-1 medium (Hycor) supplemented with 2 mM L-glutamine. $10^6$ LN cells/well were plated onto 96 wells microtiter plates (TPP, Tresedingen, Switzerland) with 10 µg/ml of the indicated antigen or medium alone. After 3 days at 37° C., cells were pulsed for 18 h with $^3$H-TdR (NEN, Boston, Mass.) and then harvested onto fiber glass filters (Wallac Oy, Turku, Finland) with an automated cell harvester. Incorporated radioactivity was measured by scintillation counting. Results were expressed as mean of cpm from duplicate or triplicate culture wells. Standard deviations were less than 15% of the mean.

ELISA Tests:

Desialylated OSM was prepared as described in a previous publication (Ref. 32) and was kindely given by Dr A. Babino.

a-GalNAc-Ser (referred to as 3 below in the synthesis section) was covalently linked to ovalbumin (Sigma, St Louis, Mo.) using glutaraldehyde (Sigma) according to a known procedure (Ref. 33).

96-well microtiter plates (Nunc, Roskilde, Denmark) were coated with 10 µg per ml of the different antigens in 50 mM carbonate buffer pH 9.6 and incubated overnight at 4° C. for d-OSM, ovalbumin and Ova-Tn glycoconjugate, or at 37° C. for peptides and MAG constructs. After washing with PBS containing 0.1% TWEEN 20 (polyoxvethylene (20) sorbitan monolaurate , the 83D4 (IgM) or the MLS 128 (IgG) anti-Tn mAbs were diluted in buffer (PBS plus 0.1% TWEEN 20 (polyoxyethylene (20) sorbitan monolaurate), 1% BSA) and plated respectively at 2.5 µg/ml and 40 µg/ml for 1 hour at 37° C. Following three washes, wells were treated for 1 hour at 37° C. with goat anti-mouse IgM or anti-IgG peroxydase conjugate (Sigma, St. Louis, Mo.) and O-phenylenediamine/$H_2O_2$ was then added as substrate. Plates were read photometrically at 492 nm in an ELISA auto-reader (Dynatech, Marnes la Coquette, France).

Analysis of Antibody Response:

BALB/c mice (5 per group) were immunized intraperitoneally with 20 µg of T, B-T, T4-MAP, B4-MAP or B4-T4-MAP compound in aluminium hydroxyde (alum) on days 0, 20, 42 and 63. Mice were bled 10 days after each immunization and collected sera were individually tested for anti-Tn antibodies by ELISA as described above using d-OSM coated plates. Sera were serially diluted and tested for anti-Tn IgM and IgG content. The negative control consists of naive mouse sera diluted 100-fold. ELISA antibody titers were determined by linear regression analysis plotting dilution versus absorbance at 492 nm. The titers were calculated to be the Log10 highest dilution which gave twice the absorbance of normal sera diluted 1/100. Titers were given as the arithmetic mean+S.D. of the Log10 titers. Statistical analysis was performed by Student's t test. P values less than 0.05 were considered significant.

1) In vitro Antiqenicity of B4-T4-M

In vitro recognition of the B4-T4-M by a T hybridoma specific for the poliovirus 103-115 epitope T was assayed in the presence of lymphoma B, A20, as antigen presenting cell.

Figure 4A:
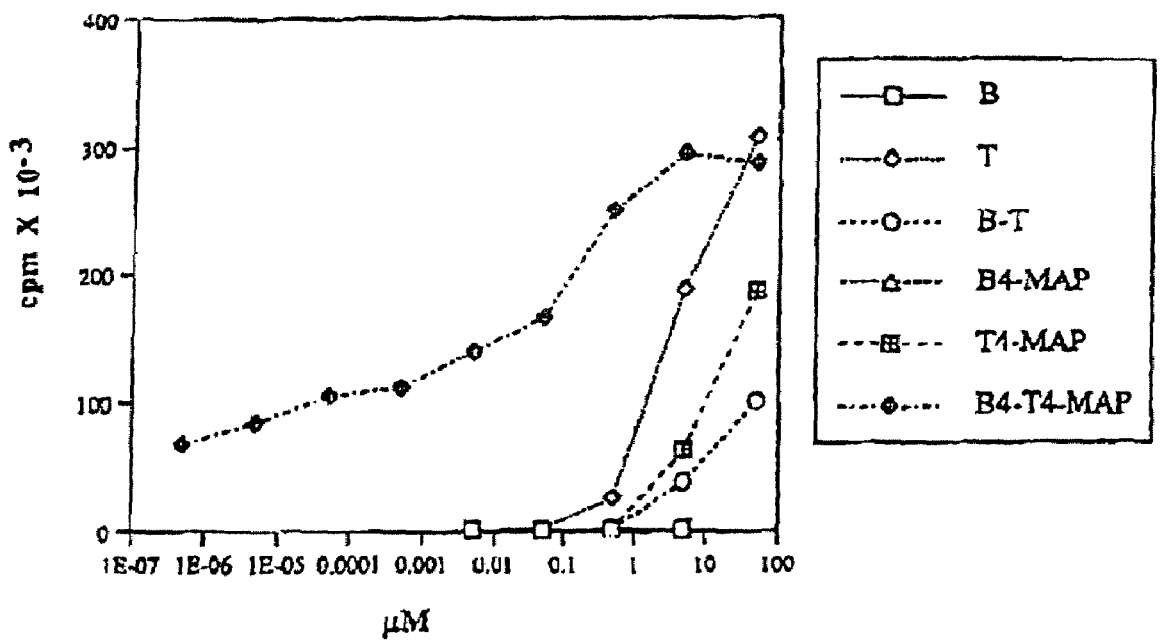
FIG. 4a depicts the T antigenicity of B4-T4-M in vitro.
Figure 4B:
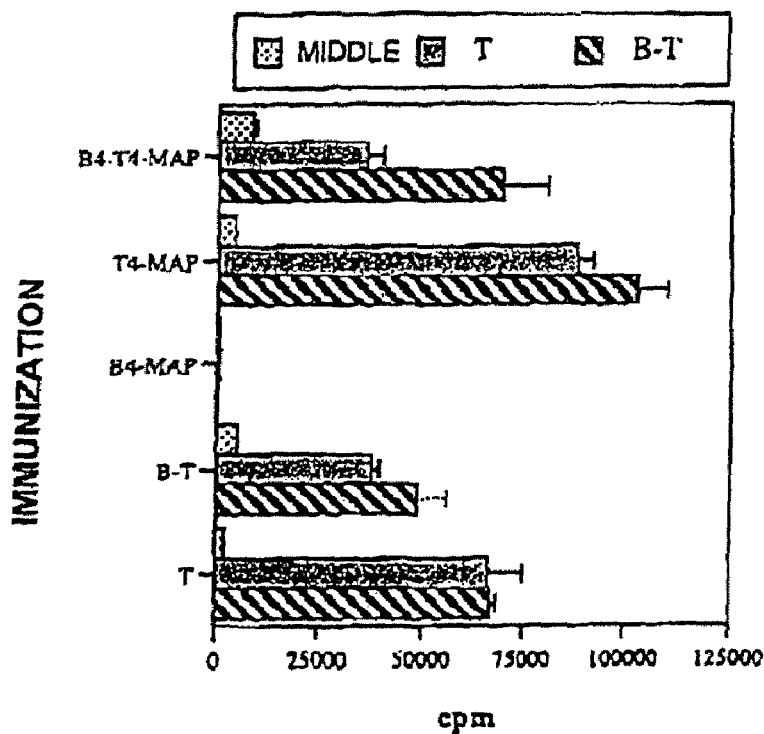
FIG. 4b illustrates the in vivo anti-T response of B4-T4-M.
Figure 5:
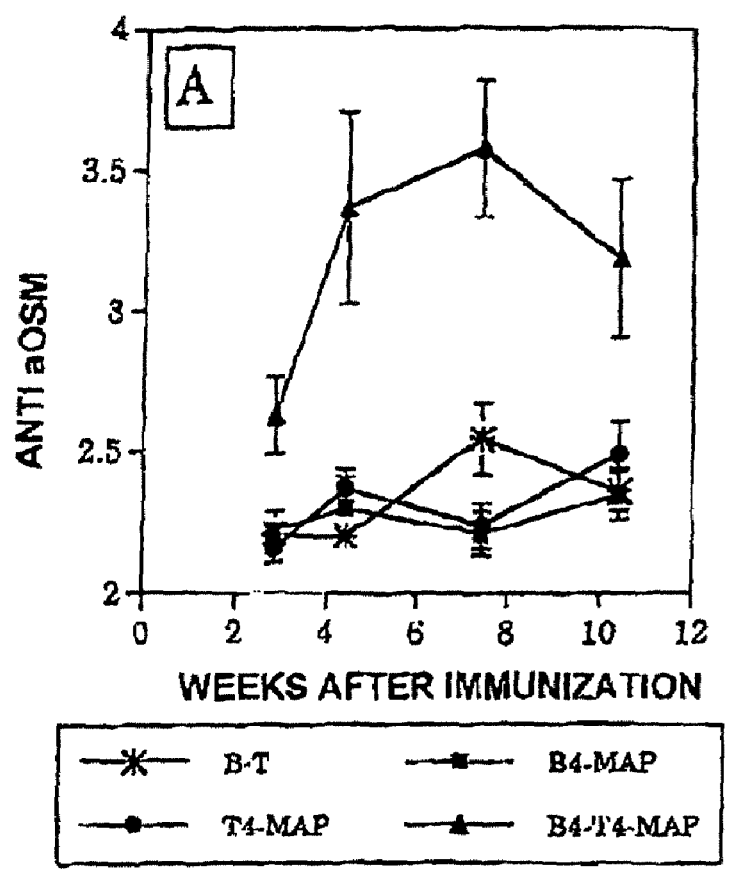
FIGS. 5a, 5b and 5c show the induction in BALB/c, SJL/J and DBA/1 mice, respectively, of anti-Tn antibody by the Tn-MAG compound.
Figure 5:
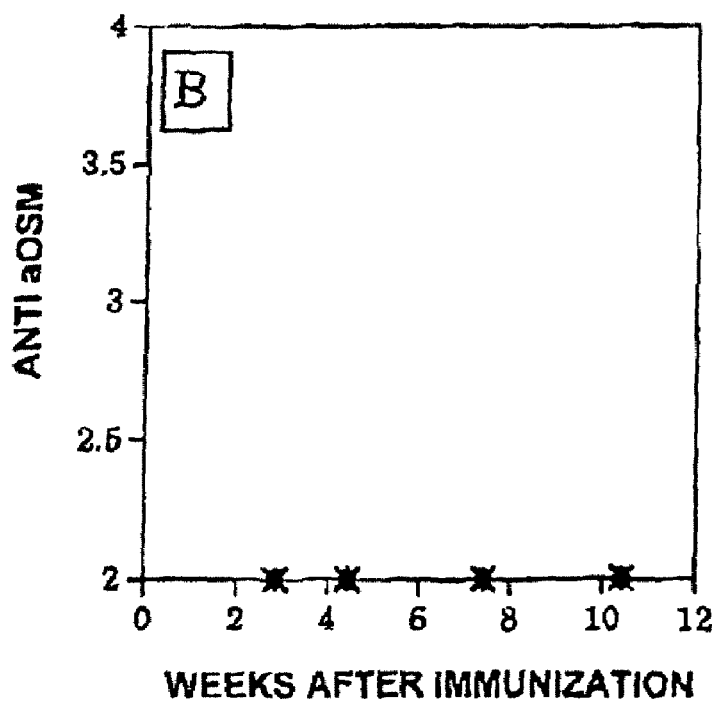
Figure 5B:
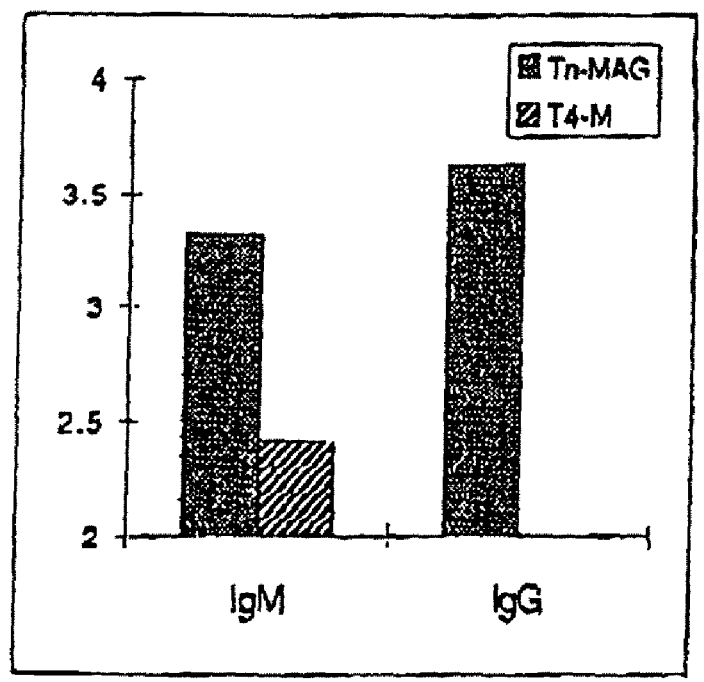
Figure 5C:
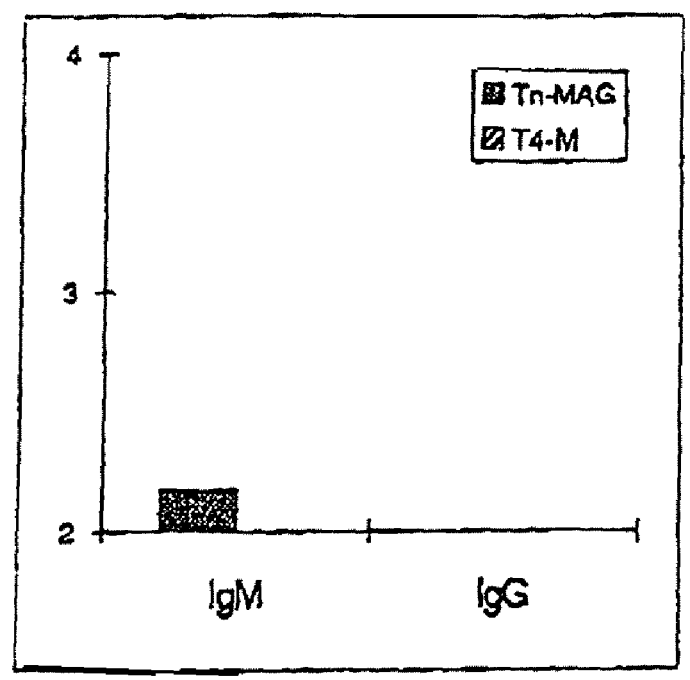

FIG. 4a illustrates the stimulation of a T hybridoma specific for the poliovirus peptide 103-115 T with different compounds containing this peptile:

$10^5$ lymphoma B.A20 (H-2$^d$) cells incubated at 37° C., in the presence of different concentrations of B, T, B-T, B4-MAP, T4-MAP and B4-T4-MAP were used for stimulating $10^5$ cells of T,45G10 hybridoma (R. Lo-Man et al. (1994). 152: 5660-5669) specific for poliovirus 103-115 peptide and restricted by I-A$^d$ molecules. After 24 h, the culture supernatants were sampled then IL-2 was assayed by the measure of the proliferation of IL-2 dependent CTLL line. After three days of culture, the proliferation of CTLL cells was measured by tritiated thymidine incorporation. The results are expressed in cpm.

As can be seen on FIG. 4a, the B4-T4-MAP compound highly stimulates the IL-2 production by the T hybridoma specific for the T epitope. Compared to the other compounds T, B-T, T4-MAP also containing epitope T, the antigenicity of the conjugate of the present invention, compound B4-T4-MAP, is 100 to 1000 times higher. The B and B4-MAP compounds which are free of poliovirus epitope T do not stimulate the T hybridoma.

Then the in vivo T immunogenicity of the epitope T of the present invention conjugate, B4-T4-MAP, was assayed in BALB/c mice. After the immunization of mice with the B4-T4-MAP, or with a control compound (T, B-T, B4-MAP, T4-MAP). the proliferation of lymph node cells was measured in vitro after restimulation with compounds containing T epitope alone or in combination with B epitope (T and B-T compounds).

The FIG. 4*b* illustrates the induction of a proliferative response specific for 103-115 peptide (T compound) after immunization of BALB/c mice with the B4-T4-MAP compound according to the present invention. BAL.B/c (H-$2^d$) mice were immunized subcutaneously with 10 μg of T, B-T B4-MAP, T4-MAP and B4-T4-MAP in the presence of complete Freund adjuvant. Ten days later, draining lymph node cells were cultured in the presence of the medium alone or were restimulated in vitro with 10 μg/ml of a compound containing the 103-115 epitope (compound T or B-T). Four days later, the proliferation of LN cells was measured by incorporation of tritiated thyrmidine. The results were expressed in cpm.

As can be seen on FIG. 4*b*, the MAPs, B4-T4-MAP and T4-MAP compounds, as well as the T and B-T compounds containing the T epitope, induce in vivo a proliferative T response specific for this T epitope. The specificity of the T response observed is demonstrated by the absence of proliferation of T cells originating from mice immunized with B4-MAP compound which is free of T epitope, after restimulating with T or B-T compounds.

Thus it was possible to show through the analysis of the T immunogenicity of the conjugate according to the present invention (the B4-T4-MAP compound) that the poliovirus T epitope present in this compound is able to stimulate both in vitro and in vivo T-cells specific for this T epitope. Moreover a large increase in antigenicity of the T epitope is observed when the latter is combined to the carbohydrate epitope within the B4-T4-MAP structure.

2) Antigenicity of the B4-T4-MAP Structure 2.1 To assess the antgenicity of the Tn antigen in the glycoconjugate MAG system according to the invention, we have used two different well-characterized monoclonal antibodies (mAbs) which recognize the Tn antigen. FIG. 3 shows the binding ability of the anti-Tn 83 D4 (IgM) (Ref. 26) and MLS 128 (IgG) (Ref. 27) monoclonal antibodies to the different MAG constructs using an ELISA assay. This binding is compared to the binding obtained with the Tn antigen 3 conjugated to a protein carrier (ovalbumin).

Fully synthetic multiple antigenic glycopeptides allow to a certain degree the rejection of an implanted tumour bearing aberrant glycosylations. However, to induce more efficient anti-tumour immunity against cancers, the development of such immunuogens should not focus on a single carbohydrate antigen but must combine various carbohydrate targets for antibodies. The use of a given The cell epitope in conjunction with carbohydrates is a prerequisite for eliciting strong antibody responses, but it may limit its efficacy considering the MHC polymorphism observed in the human population. To avoid this drawback, MAG structures have to include several T cell epitopes with a particular focus on promiscuous MHC binding sequences, such as those described for tetanus toxin (Ref. 41, Ref. 42) for which human individuals are already primed (Ref 43). Integration of CTL epitopes into MAG structures, such as MUC-1 derived peptides (Ref. 44) for epithelial cancers, can also be easily achieved to widen the spectrum of the anti-tumour immune response. Here, we have privileged the use of a mild adjuvant, alum, which is authorized in healthy human populations, showing that strong adjuvants are not required to induce anti-carbohydrate specific immune responses by the MAG strategy. This latter point may be of major importance in extending the use of this strategy to bacterial oligosaccharides (Ref. 46) for vaccinating a healthy population.

It can be seen that the B4-T4-M system of the invention as well as the desialylated OSM or the ovalbumin-Tn (Ova-Tn) conjugate were efficiently recognized by both of the mAbs, 83 D4 and MLS 128, whereas M, B4-M, T4-M, B-T (in the last case, only one mAb was tested) and ovalbumin itself were not. The d-OSM fragment recognized by MLS 128 monoclonal antibody was shown to contain three consecutive a-GalNAc-Ser/Thr residues (Ref. 28) which might indicate that B4-T4-M but not B4-M is able to mimic the repeated glycosylated serine unit.

These results demonstrate that the B4-T4-M construct according to the invention can correctly present the Tn antigen.

2.2 Another study of the immunogenicity in mice of Tn-MAG conjugates of the invention was first carried on BALB/c mice which were immunized several times with said Tn-MAG conjugates or with the control compounds B-T, B4-MAP or T4-MAP, in the presence of aluminium hydroxyde (alum). Detection of IgM (FIG. 5*a*) and IgG (FIG. 5*b*) antibodies specific for Tn antigen was carried out by ELISA, measuring the recognition of the d-OSM.

As can be seen on FIGS. 6*a* and 5*b*, after two immunizations with the B4-T4-MAP compound according to the invention, IgM antibodies specific for the Tn antigen were induced in BALB/c mice, unlike compounds B-T, B4-MAP or T4-MAP which were unable to induce anti-Tn antibodies. The amount of anti-Tn IgM induced with B4-T4-MAP remained unchanged after a third and a fourth immunization. With BALB/c mice it appeared that the antibody response to Tn induced by B4-T4-MAP was characterized by the presence of IgM antibodies and the absence of IgG antibodies.

2.3 A further study of induction of anti-Tn antibodies under the same conditions was conducted on another strain of mice of $H2^s$ haplotype (responding to the T epitope) namely SLJ/J mice, and resulted in the inducton of both class IgM and IgG antibodies to Tn (FIG. 5*b*). Thus, the B4-T4-MAP (Tn-MAG) compound of the present invention was capable of inducing antibodies to Tn belonging to different isotypes, the reason why there exist differences in the anti-in antibody class depending on the tested mouse strain is still under study.

The $CD4^+$ T-cell dependency of the Tn-MAGC compound B immunogenicity was also studied. As stated above, BALB/c mice are responsive to the poliovirus T epitope and generate antibodies to Tn. In order to determine the T-dependency of the production of anti-Tn antibodies, we assayed for their capacity to produce antibodies to Tn another mouse strain responsive to poliovirus epitope T, namely the SLJ/J strain, and a non responsive to poliovirus epitope T strain namely the DBA/1 strain.

FIGS. 5*b* and 5*c* show that immunization with the Tn-MAG compound, according to the present invention, of SLJ/J (5*b*) and DBA/1 (5*c*) mice resulted in the production of anti-Tn antibodies in the SLJ/J strain only, which is responsive to the poliovirus T epitope. These data demonstrate that the CD4+.T epitope present in the Tn-MAG compound of the present invention is necessary to the production of antibodies to Tn.

2.4 We further studied the induction of anti-peptide antibodies using the Tn-MAG compound of the present invention.

Figure 6:
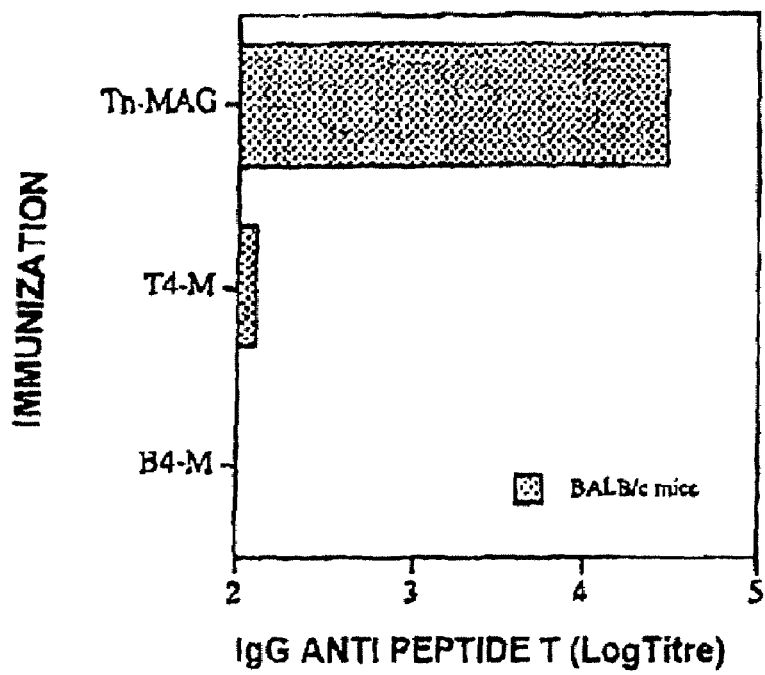
FIG. 6 illustrates the induction in BALB/c mice of antibody responses by the Tn-MAG compound containing Tn antigen and poliovirus epitope T. CD4+.

As stated above the conjugate of the present invention (Tn-MAG compound) contains four copies of the 103-115 sequence of VP1 protein of pollovirus type 1 (T peptide). linked to the carbohydrate Tn antigen. We have tested in mice the ability of the Tn-MAG compound to induce antibodies specific for the T peptide. As shown in FIG. 6. Immunization of BALB/c mice with the Tn-MAG of the present invention induced a strong IgG response specific for the T peptide (103-115), whereas the T4-M compound lacking the carbohydrate Tn antigen, as well as the B4-M compound containing only the Tn antigen, were unable to elicit an anti-T peptide antibody response. Therefore, the presence of the carbohydrate moiety in the conjugate Tn-MAG of the present invention, results in a strong potentiating effect on the induction of anti-peptide antibodies against the peptidic poliovirus contained in the MAG compound. These data suggest that such a carbohydrate peptide conjugate can he used to promote anti-peptide response generally in MAP synthetic compounds containing pathogen derived peptidic sequences.

Example 3

Figure 7:
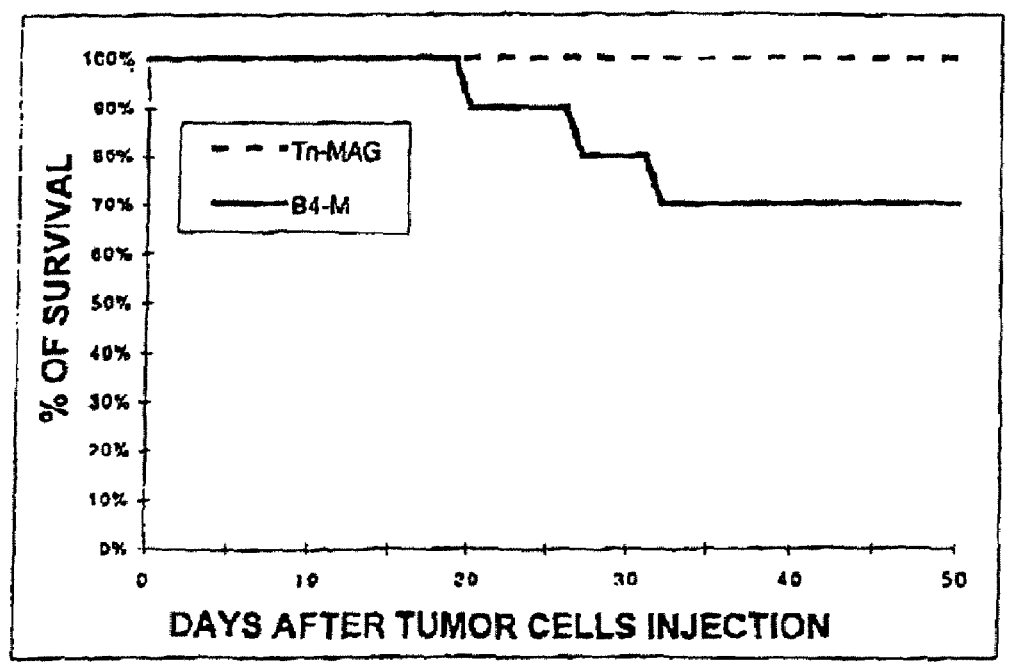
FIG. 7 illustrates the results of the protection induced with the Tn-MAG compound against murine adenocarcinoma TA3/Ha expressing Tn antigen in challenge injected BALB/c mice.

Protection Induced with the Conjugate of the Present Invention (Tn-MAG Compound) Against Murine Adenocarcinoma TA3/Ha Expressing Tn Antigen in Challenge Injected BALB/c Mice In order to test the efficiency of the anti-Tn B response induced in mice with the MAG compound, a challenge injection was carried out in vaccinated mice. 1000 cells per mouse of the murine adenocarcinoma cell, TA3/Ha (P. Y. S. Fung et al. (1990) Cancer Research. 50: 4308-4314), expressing Tn antigen, were intraperitoneally administered to BALB/c mice having received 4 injections of the B4-M or Tn-MAG compounds. The FIG. 7 is a graph illustrating the mortality versus the number of days after tumor challenge. BALB/c mice were immunized at days 0, 21, 42 and 100 with 20 µg of B4-M or Tn-MAG compound in the presence of alum. 15 days after, the mice received a challenge injection of 1000 TA3/Ha adenocarcinoma cells. The mortality was followed during a period of 50 days. As can be seen in FIG. 7, 70% only of the mice survived when these were immunized with B4-M compound which does not allow to induce an antibody to Tn. On the contrary, 100% of the mice having received four injections of the conjugate of the present invention survived at D50 after the tumor challenge. These data show that the antibodies induced with Tn compound of the present invention result in improving the mice survival after a tumor challenge causing a moderate lethality.

Example 4

Recognition of a Human Adenocarcinoma by Antibodies Originating from a Serum of a Mouse Immunized with the Conjugate of the Present Invention (Tn-MAG Compound)

In order to evaluate the possible human applications of the conjugate of the present invention the sera of mice having received the latter were assayed for their ability to recognize a human tumor cell. For this purpose. we used the LS180 cell (ATCC CL-187) which a adenocarcinoma derived from a patient having developed a colon cancer. A flow cytometry analysis of the recognition of LS180cell by a serum originating from a SLJ/J mouse having received three injections of the present conjugate (Tn-MAG) show that the induced anti-Tn antibodies are capable of recognizing Tn antigen at the surface of LS180 cells.

Example 5

Synthesis of a Linear Glycopeptide Containing a CD4+ T Cell Epitope Asscociated with a Saccharidic Antigen to Induce Anti-saccharidic Antibodies.

The basic compound to induce anti-saccharidic antibodies is a linear peptidic sequence containing a CD4+ T cell epitope linked to a saccharidic chain. The BT compound is composed by the KLFAVWKITYKDT (SEQ ID NO: 4) sequence derived from poliovirus type 1 (CD4+ T cell epitope) linked at the N-terminus to three GalNac-Ser/Thr residues (tumor associated saccharidic Tn antigen). The BT compound or the control PV peptide, sequence KLFAVWKITYKD (SEQ ID NO: 4) was injected to BALB/c mice mixed with complete Freund's adjuvant or with alum as follows.

BALB/c mice (5 per group) were immunized in CFA or Alum with either the B-T-PV or the control peptide PV on days 0, 21, 42, 63. Sera were collected 10 days after the last injection and tested in ELISA for antibody titer against the B-T-TT1 glycopeptide or the TT1 peptide. Results are expressed in FIG. 8 as the mean titer obtained for five mice in each group.

Figure 8A:
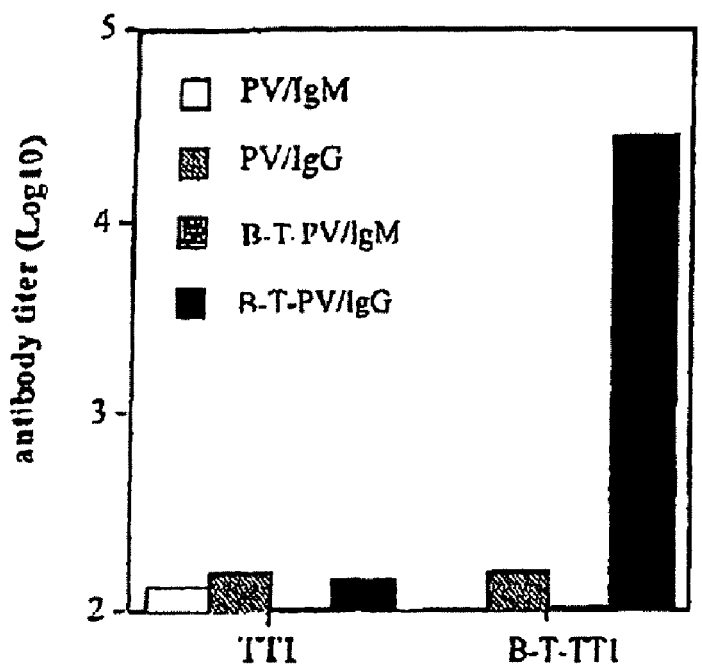
FIGS. 8A and 8B illustrate the results of immunization of Balb/C mice with the TT1 peptide or B-T-TI$_i$ glycopeptide, respectively primed with CFA (FIG. 8A) and with alum (FIG. 8B).
Figure 8B:
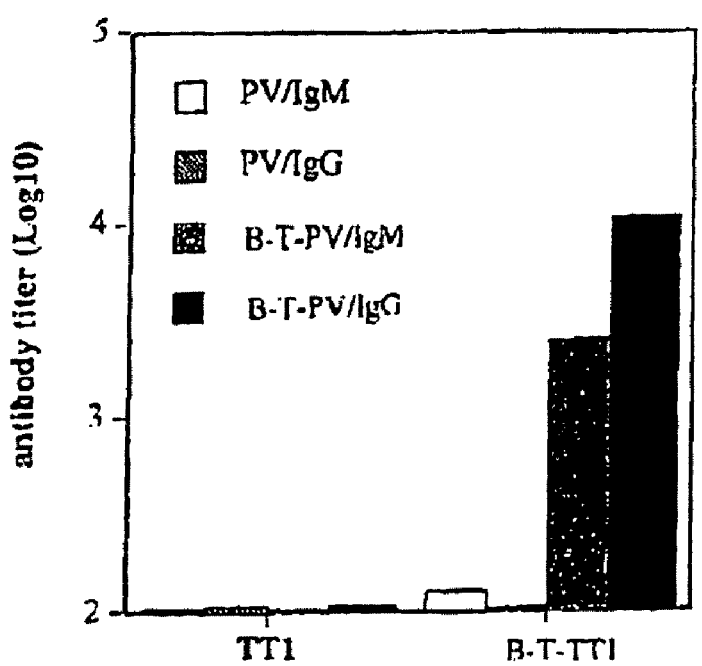

To detect by ELISA anti-saccharidic antibodies (anti-Tn), an irrelevant peptide sequence QYIKANQKFIIGITEL (SEQ ID NO: 5) linked at the N-terminus to three GalNac-Ser/Thr residues (BT-TT1) was used, or the non glycosylated YIKANSKFIIGITEL (SEQ ID NO:6) (TT1 peptide) as a negative control. As shown in FIG. 8, the B-T-PV glycopeptide induce anti-Tn antibodies, but not the PV peptide showing the specificity of the antibody response.

These results demonstrate that a synthetic linear glycopeptide containing a saccharidic B cell epitope and a CD4+ T cell epitope is able to induce anti-saccharidic antibodies.

Although only preferred embodiments are specifically illustrated and described herein it will be appreciated that many modifications and variations of the present invention are possible in the light of the above teachings and within purview of the following appended claims without departing from the spirit and intended scope of the invention.

TABLE

| Synthetic compounds and glycoproteins | | |
|---|---|---|
| | Copy number per molecule | |
| Antigen designation | αGalNac-Ser (Tn antigen) | peptide 103-115 (1 epitope) |
| T | 0 | 1 |
| B | 1 | 0 |
| B-T | 1 | 1 |
| M or MAP | 0 | 0 |
| B4-M | 4 | 0 |
| T4-M | 0 | 4 |
| B4-T4-M or Tn-MAG | 4 | 4 |
| Ovalbumin | 0 | 0 |
| Ovalbumin-Tn | ++* | 0 |
| d-OSM | ++* | 0 |

*several copies but copy number not determined.

REFERENCES 1. a) Bhavanandan, V. P. (1991) *Glycobiology* 1, 493-503; b) Hakomori, S. (1989) *Adv. Cancer Res.* 52, 257-331; c) Fukuda, M. (1996) *Cancer Res.* 56, 2237-2244.

2. MacLean, G. D., Reddish, M. A., Bowen-Yacyshyn, M. B., Poppema, S., Longenecker, B. M. (1994) *Cancer Invest.* 12, 46-56.
3. a) Springer, G. F. (1984) *Science* 224, 1198-1206; b) Itzkowitz, S. H., Yuan, M., Montgomery, C. K., Kjeldsen, T., Takahashi, H. K., Bigbee, W. L., Kim Y. S. (1989) *Cancer Res.* 49, 197-204: c) Springer, G. F. (1995) *Crit. Rev. Oncogen.* 6, 57-85; (d) Yamashita, Y., Chung, Y. S., Horie, R., Kannagi, R., Sowa, M. (1995) *J. Natl. Cancer Inst.* 87, 441-446.
4. Springer, G. F., Desai, P. R., Tegtmeyer, H., Carlstedt, S. C., Scanlon, E. F. (1994) *Cancer Biother.* 9, 7-15.
5. Singhal, A., Fohn, M., Hakomori, S. (1991) *Cancer Res.* 51, 1406-1411.
6. O'Boyle., K. P., Zamore. R., Adluri, S., Cohen, A., Kemeny, N., Welt, S., Lloyd, K O., Oettgen, H. T., Old, L. J., Livingston, P. O. (1992) *Cancer Res.* 52, 5663-5667.
7. Ratcliffe, R. M., Baker, D. A., Lemieux, R. U. (1981) *Carbohydr. Res.* 93, 35-41.
8. Fung, P. Y. S., Madej. M., Koganty, R. R., Longenecker, B. M. (1990) *Cancer Res.* 50, 4308-4314.
9. MacLean, G. D., Bowen-Yacyshyn, M. B., Samuel, J., Meikle, A., Stuart, G., Nation, J., Poppema, S., Jerry, M., Koganty, R., Wong, T., Longenecker, B. M. (1992) *J. Immunotherap.* 11, 292-305.
10. Longenecker, B. M., Reddish, M., Koganty, R., MacLean, G. D. (1993) in *Specific immunotherapy of cancer with vaccines* (Bystryn, J. C., Ferrone, S., Livingston, P. Eds), Ann. N.Y. Acad. Sci. 690, 276-291.
11. Helling, F,. Zhang, S., Shang, A., Adluri, S., Calves, M., Koganty, P., Longenecker, B. M. (1995) *Cancer Res.* 55, 2783-2788.
12. (a) Toyokuni, T., Hakomoiri, S., Singhal, A. K. (1994) *Bioorg. Mod. Chem.* 2, 1119-1132; (b) Toyokuni, T., Dean. B. Cai, S., Boivin, D., Hakomori, S., Singhal, A. K. (1994) *J. Am. Chem. Soc.* 116, 395-396; c) Toyokuni, T., Singhal, A. K. (1995) *Chem. Soc. Rev.,* 231-242.
13. (a) Posnett, D. N., McGrath, H., Tam, J. P. (1988) *J. Biol. Chem.* 263, 1719-1725; (b) Tam, J. P. (1988) *Proc. Natl. Acad. Sci. USA* 85, 5409-5413.
14. Tam, J. P. (1994) in *Peptide antigens, A Practical Approach* (Wisdow, G. B. Eds), Oxford University Press, 83-115 and references cited herein
15. Leclerc, C., Deriaud, D., Mimic, V., Van der Werf, S. (1991) *J. Virol.* 65, 711-718.
16. Roy, R., Zanini, D., Romanowska, A., Meunier, S. J., Park, W. K. C., Gidney, M. A., Harrison, B., Bundle, D. R., Williams, R. E. Abstract of poster, XIII International Carbohydrate Symposium (17-22 Jul. 1994).
17. Lett, E., Klopfenstein, C., Klein, J-P., Schöller, M., Wachsmann, D. (1995) *Infect. Immun.* 63, 2645-2651.
18. Tam, J. P., Clavijo, P., Lu, Y., Nussenzweig, V., Nussenzweig, R., Zavala, F. (1990) *J. Exp. Med.* 171, 299-306.
19. (a) Paulsen, H., Hölck, J-P. (1982) *Carbohydr. Res.* 109, 89-107; (b) Paulsen, H., Schultz, M., Klamann, J-D., Waller, B., Paal, M. (1985) *Liebigs Ann. Chem.* 2028-2048.
20. Paulsen, H., Adermann, K. (1989) *Liebigs Ann. Chem.* 751-759.
21. Shafizadeh, F. (1963) *Methods Carbohydr. Chem.* 2, 409-410.
22. a) Vowinkel, E. (1967) *Chem. Bor.* 100, 16-22 b) Schultz, M., Kunz, H. (1993) *Tetrahedron Assym.* 4, 1205-1220.
23. (a) Lemieux, R. U., Ratcliffe, R. M. (1979) *Can. J. Chem.* 57, 1244-1251: (b) Ferrari, B., Pavia, A. A. (1980) *Carbohydr. Res.* 79, C1-C7.
24. (a) Filira, T., Giondi, L., Covaggion, F., Scolaro, B., Rocchi, R. (1990) *Int. J. Peptide Protein Res.* 36, 86-96, (b) Otvos, L., Urge, L., Hollosi, M., Wroblewski, K., Graczyk, G., Fasman, G. D., Thurin, J. (1990) *Tetrahedron Lett.* 31, 5889-5892.
25. a) Paulsen, H., Merz, G., Weichert, U. (1988) *Angew. Chem. Int. Ed. Engl.* 27, 1365-1367; b) Jansson, A. M., Meidal, M., Bock, K.(1990) *Tetrahedron. Lett.* 31, 6991-6994; c) Peters, S., Bielfeldt, T., meidal, M., Bock, K., Paulsen, H. (1992) *Tetrehedron Lett.* 33, 6445-6448.
26. Pancino, G., Osinaga, E., Vorauher, W., Kakouche A., Mistro, D., Charpin, C., Roseto, A (1990) *Hybridoma* 9, 389-395.
27. Numata, Y., Nakada, H., Fukui, S., Kitagawa, H., Ozaki, K., Inoue, M., Kawasaki, T., Funakoshi, I., Yamashina, I. (1990) *Biochem. Biophys. Res. Commun.* 170, 981-985.
28. Nakada, H., Numata, Y., Inoue, M., Tanaka, N., Kitagawa, H., Funakoshi, I., Fukui, S., Yamashina, I. (1991) *J. Biol. Chem.* 266, 12402-12405.
29. Kaiser. E., Colescott, R. L. Bossinger, C. D., Cook, P. I. (1980) *Anal. Biochem.* 34, 595-598.
30. Walker, B. (1994) in Peptide antigens (Wisdow, G. B. Eds), Oxford University Press, The Practical Approach Series, 27-81.
31. Meienhofer, J., Waki, M., Heimer, E. P., Lambros, T. J., Makofske, R. C., Chang, C. D. (1970) *Int. J. Pept. Protein Res.* 13, 35-42.
32. (a) Tettamant G., Pigman, W. (1968) *Arch. Biochem. Biophys.* 124, 41-50; (b) Osinaga, E., Babino, A., Grosclaude, J., Cairoli, E., Batthyany, C., Bianchi, S., Signorelli, S., Varangot, M., Musé, I., Roseto, A. (1996) *Int. J. Oncol.* 8, 401-406.
33. Leclerc, C., Sedlik, C., Lo-Man, R., Charlot, B., Rojas, M., Deriaud. E. (1995) *Eur. J. Immunol.* 25, 2533-2538.
34. Itzkowitz, S. H., et al. Sialosyl-Tn. A novel mucin antigen associated with prognosis in colorectal cancer patients. *Cancer* 66, 1960-6 (1990).
35. Deshpande, P. P. & Danishetsky, S. J. Total synthesis of the potential anticancer vaccine kh-1 adenocarcinoma antigen, *Nature* 387, 164-166 (1997).
36. Sames, D., Chen, X. T. & Danishefsky, S. J. Convergent total synthesis of a tumour-associated mucin motif, *Nature* 389, 587-591 (1997).
37. Herzenberg, L. A., Tokuhisa, T. & Herzenberg, L. A. Carrier-priming leads to hapten-specific suppression, *Nature* 285, 664-7 (1980).
38. Schutze, M. P., Leclerc, C., Jolivet, M., Audibert, F. & Chedid, L. Carrier-induced epitopic suppression, a major issue for future synthetic vaccines, *J. Immunol.* 135, 2319-22 (1985).
39. Kim, Y. J. & Varki, A. Porspectives on the significance of altered glycosylation of glycoproteins in cancer. *Glycoconj. J.* 14, 559-576 (1997).
40. Bay, S., et al. Preparation of a multiple anitigen glycopeptide (MAG) carrying the In antigen—a possible approach to a synthetic carbohydrate vaccine, *J. Pep. Res.* 49, 620-625 (1997).
41, Panina-Bordignon, P., et al. Universal immunogenic T cell epitopes: promiscuous binding to human MHC class II and promiscuous recognition by T cells. *Eur. J. Immunol* 19, 2237-2242 (1989).
42. Reece, J. C., Geysen, H. M. & Rodda, S. J. Mapping the major human T helper epitopes of tetanus toxin. The emerging picture. *J. Immunol.* 151, 6175-6184 (1993).
43. Etlinger, H. M., et al. Use of prior vaccinations for the development of new vaccines, *Science* 249, 423-5 (1990).
44. Goydos, J. S., Elder, E., Whiteside, T. L., Finn, O. J, & Lotze, M. T. A phase I trial of a synthetic mucin peptide vaccine. Induction of specific immune reactivity in patients with adenocarcinoma. *J. Surg. Res.* 63, 298-304 (1996).
45. Chong, P., et al. A strategy for rational design of fully synthetic glycopeptide conjugate vaccines. *Infect. Immun.* 65, 4918-4925 (1997).

What is claimed is:

1. A method for obtaining antibodies directed against a carbohydrate moiety (B) contained in a carbohydrate peptide conjugate, comprising:

a) administering to a human or an animal body a composition comprising a carbohydrate peptide conjugate having a carbohydrate content ranging from 33% (w/w) to 90% (w/w), said conjugate being selected from the group of conjugates of formulae (a) to (f) below:

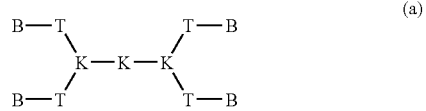

(a)

-continued

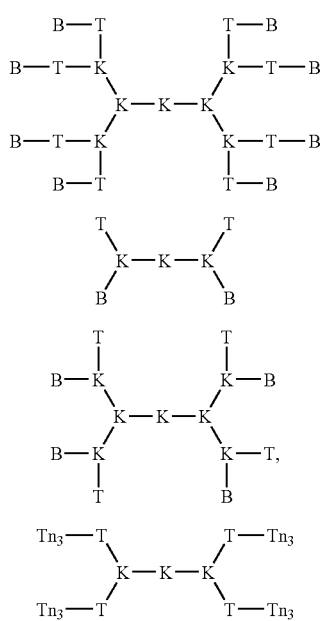

(b)

(c)

(d)

(e)

-continued

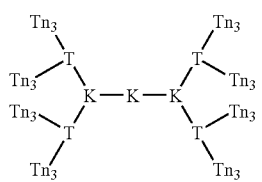

(f)

wherein:

K is a lysyl residue,

T is a CD4$^+$ T cell epitope, and

B and Tn is a Tn antigen selected from the group consisting of α-Gal-Nac-Ser, α-Gal-Nac-Thr, β-Gal-(1-3)-α-Gal-Nac-Ser, β-Gal(1-3)α-Gal-Nac-Thr(α-Gal-Nac-Ser/Thr)$_2$, (α-Gal-Nac-Ser/Thr)$_3$ and (α-Gal-Nac-Ser/Thr)$_6$; and b) collecting the antibodies directed against the said carbohydrate moiety (B) from a serum obtained from said human or animal body.

* * * * *